US012144661B2

(12) United States Patent
Saphier et al.

(10) Patent No.: US 12,144,661 B2
(45) Date of Patent: Nov. 19, 2024

(54) GESTURE CONTROL USING AN INTRAORAL SCANNER

(71) Applicant: Align Technology, Inc., San Jose, CA (US)

(72) Inventors: Ofer Saphier, Rehovot (IL); Eliran Dafna, Beer-sheva (IL); Tal Levy, Rehovot (IL)

(73) Assignee: Align Technology, Inc., San Jose, CA (US)

( * ) Notice: Subject to any disclaimer, the term of this patent is extended or adjusted under 35 U.S.C. 154(b) by 404 days.

(21) Appl. No.: 17/138,840

(22) Filed: Dec. 30, 2020

(65) Prior Publication Data

US 2021/0196152 A1  Jul. 1, 2021

Related U.S. Application Data

(60) Provisional application No. 62/955,947, filed on Dec. 31, 2019.

(51) Int. Cl.
*A61B 5/00* (2006.01)
*G06F 3/01* (2006.01)

(52) U.S. Cl.
CPC .......... *A61B 5/7475* (2013.01); *A61B 5/0088* (2013.01); *A61B 5/742* (2013.01); *G06F 3/017* (2013.01)

(58) Field of Classification Search
None
See application file for complete search history.

(56) References Cited

U.S. PATENT DOCUMENTS

| | | |
|---|---|---|
| 6,099,314 A | 8/2000 | Kopelman et al. |
| 6,334,772 B1 | 1/2002 | Taub et al. |
| 6,334,853 B1 | 1/2002 | Kopelman et al. |
| 6,463,344 B1 | 10/2002 | Pavlovskaia et al. |
| 6,542,249 B1 | 4/2003 | Kofman et al. |
| 6,633,789 B1 | 10/2003 | Nikolskiy et al. |
| 6,664,986 B1 | 12/2003 | Kopelman et al. |
| 6,697,164 B1 | 2/2004 | Babayoff et al. |
| 6,845,175 B2 | 1/2005 | Kopelman et al. |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,319,529 B2 | 1/2008 | Babayoff |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| 8,989,567 B1 * | 3/2015 | Pulido ............... A61B 1/00172 396/16 |
| D742,518 S | 11/2015 | Barak et al. |

(Continued)

*Primary Examiner* — Parul H Gupta
(74) *Attorney, Agent, or Firm* — Shay Glenn LLP

(57) ABSTRACT

Apparatuses (e.g., systems, devices, etc.) and method for scanning both a subject's intraoral cavity as well as detecting, using the same scanner, e.g., wand, finger gestures and executing command controls based on these detected finger gestures.

20 Claims, 4 Drawing Sheets

(56) References Cited

U.S. PATENT DOCUMENTS

| | | |
|---|---|---|
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 11,013,581 B2 | 5/2021 | Sabina et al. |
| D925,739 S | 7/2021 | Shalev et al. |
| 2007/0152984 A1* | 7/2007 | Ording ............... G06F 3/04883 345/173 |
| 2009/0147003 A1* | 6/2009 | Do ............... G06T 15/205 345/427 |
| 2015/0002391 A1* | 1/2015 | Chen ............... H04N 23/56 345/156 |
| 2015/0316996 A1* | 11/2015 | Dal Mutto ............ G06F 3/0481 345/156 |
| 2016/0259515 A1* | 9/2016 | Sabina ............... G06F 3/0346 |
| 2019/0029784 A1 | 1/2019 | Moalem et al. |
| 2019/0388193 A1 | 12/2019 | Saphier et al. |
| 2019/0388194 A1 | 12/2019 | Atiya et al. |
| 2020/0281700 A1 | 9/2020 | Kopelman et al. |
| 2020/0281702 A1 | 9/2020 | Kopelman et al. |
| 2020/0315434 A1 | 10/2020 | Kopelman et al. |
| 2020/0349698 A1 | 11/2020 | Minchenkov et al. |
| 2020/0349705 A1 | 11/2020 | Minchenkov et al. |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068773 A1 | 3/2021 | Moshe et al. |
| 2021/0121049 A1 | 4/2021 | Rudnitsky et al. |
| 2021/0128281 A1 | 5/2021 | Peleg |
| 2021/0137653 A1 | 5/2021 | Saphier et al. |

* cited by examiner

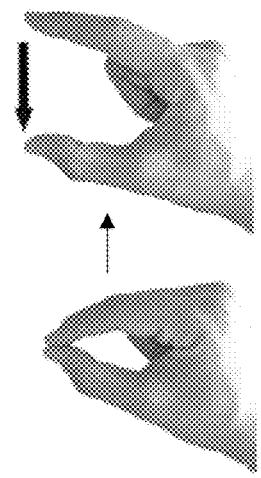 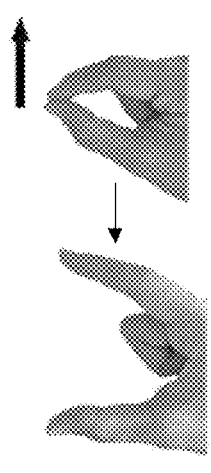 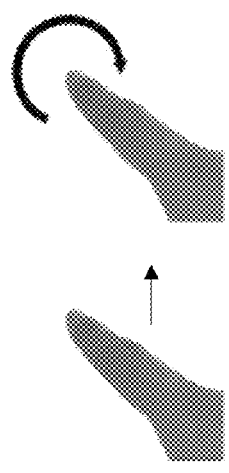 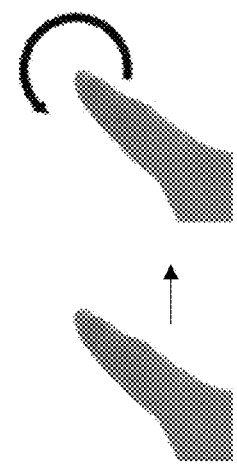
FIG. 3A     FIG. 3B     FIG. 3C     FIG. 3D
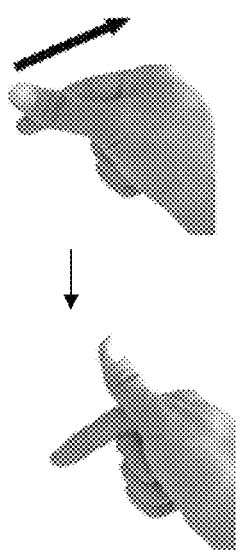 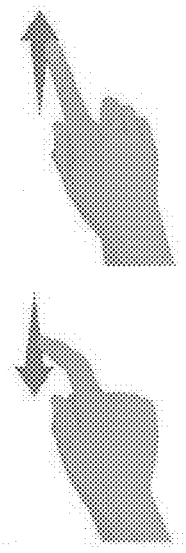 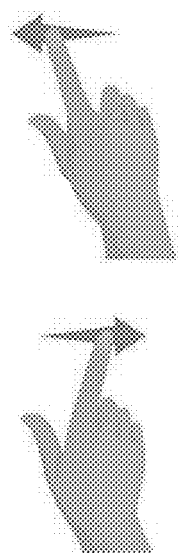 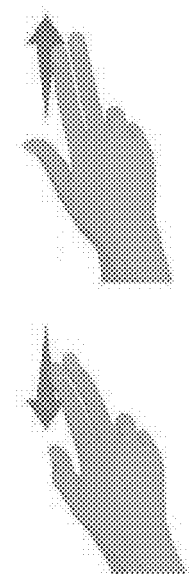
FIG. 3E     FIG. 3F     FIG. 3G     FIG. 3H
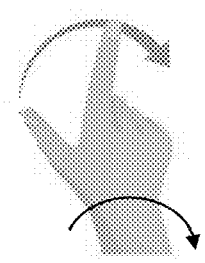
FIG. 3I

GESTURE CONTROL USING AN INTRAORAL SCANNER

CLAIM OF PRIORITY

This application claims priority to U.S. Provisional Patent Application No. 62/955,947 filed on Dec. 31, 2019, titled "GESTURE CONTROL USING AN INTRAORAL SCANNER," herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are apparatuses (e.g., systems, devices, etc.) and methods for receiving gestural control input(s) using an intraoral scanner that is may be used to scan an intra oral cavity; these gestural controls may be used to control the intraoral scanning system (including the intraoral scanner) and may aid in prosthodontic and orthodontic procedures. In particular, the apparatuses and methods described herein relate to computerized systems and methods that are that may be used for both intraoral scanning and gestural control.

BACKGROUND

In dental and orthodontic procedures, it is beneficial to accurately and carefully measure the intraoral cavity, so that the dental procedure can be properly designed and any orthodontic appliances may be properly dimensioned to fit in place. Generally, during an intraoral scan, the user (e.g., doctor, technician, etc.) must interface with the scanning system of the intraoral scanner to provide control inputs. For example, the user may operate the scanning system through a control interface that may allow manipulation of the intraoral scanner itself, and/or manipulation of the resulting images, including 2D and/or 3D models. For example, the user may alter the view of the scan during or after scanning, including zooming and/or rotating the view on the display.

This control and manipulation is typically done by a touch screen. Unfortunately, using a touch screen may create a possible source of cross-contamination, and requires cleaning of the screen between patients, adding time and cost to the procedure. Described herein are apparatuses (including systems and devices, and in particular intraoral scanning systems) that may address these issues.

SUMMARY OF THE DISCLOSURE

The methods and apparatuses described are configured to allow gesture control of an intraoral scanning system and/or of manipulation of two-dimensional (2D) or three-dimensional (3D) scans. In particular, these systems and apparatuses may permit control and manipulation of intraoral scanners and/or the data collected by the intraoral scanner using gestural control that is detected by the intraoral scanner itself, without requiring a separate gestural control (e.g., imaging) sensor.

Thus, in some examples, the methods and apparatuses described herein may use the intraoral scanner itself (including, e.g., the wand, processor(s), and in some examples a sleeve) as part of the gesture sub-system of the intraoral scanner to receive and interpret control gestures. The 2D and 3D cameras of the scanner may be configured to identify hand/finger poses and/or motions (e.g., gestures). In some examples the user may hold the intraoral scanner wand in one hand, point its camera regions at the figures of the other hand, and identify a set of gesture (pinch/zoom, pan, rotate, etc.) to control the 3D model.

In some examples the method or apparatus may display the gestural images (e.g., images of the hand and/or figures and/or a representation of the fingers and/or hand), optionally in real time, and/or the identified gesture(s). For example, images of the hand and/or fingers and/or the identified gesture may be displayed in a small windows on the screen, which may allow for confirmation and/or training.

Described herein are methods, including methods for controlling the system, and in particular, methods for controlling the display of a system during operation of an intraoral scan. For example, a method may include: scanning a subject's intraoral cavity with an intraoral scanner of an intraoral scanning system; scanning a user's finger gesture with the same intraoral scanner; executing a command control with the intraoral scanning system encoded by the user's finger gesture. As will be described in greater detail below, also described herein are apparatuses (e.g., intraoral scanning systems) configured to perform any of these methods.

These methods may generally be performed so that the apparatus (e.g., system) may detect and execute command controls communicated by a user during routine operation of the apparatus, without having to touch a screen, keyboard, or the like, while the user's other hand may continue holding the wand. This may prevent the user for For example, described herein are methods (and apparatuses for performing them) including: scanning a subject's intraoral cavity with an intraoral scanner of an intraoral scanning system; switching the intraoral scanning system from an intraoral scanning mode to a finger gesture scanning mode; scanning a user's finger position and/or movement with the same intraoral scanner in the finger gesture scanning mode; identifying a command control corresponding to the user's finger position and/or movement; and executing the command control.

Thus, any of these methods may include detecting, using the intraoral scanner, the command control from the scanned user's finger gesture. The intraoral scanner system may detect the command control from the scanned finger gesture by matching the position and/or movement of the user's finger(s) to a library of command controls associated with the finger gesture. The user's finger gestures may be interpreted by the intraoral scanner system by one or more sub-systems that is configured to determine finger position and/or motion from one or more images taken by the sensor(s) in the wand of the intraoral scanner. For example, the controller of the intraoral scanning system may be configured to include a neural network that has been trained to recognize finger position and/or movements. Alternatively or additionally, the systems described herein may develop a model, e.g., a 3D model of the user's fingers from the scans and may determine position and/or movement of a user's fingers from the 3D model. The model may be a simplified (e.g., skeletonized, vectored, etc.) model of the user's fingers.

The position and/or movement of the user's finger gestures may be determined relative to the intraoral scanner (e.g., relative to the position and/or orientation of the wand). In some examples the position and/or movement of the user's finger gestures may be determined relative to the user's other fingers.

In general, these methods may be configured to switch between at least two modes, e.g., an intraoral scanning mode and a finger gesture scanning mode. In the intraoral scanning mode the apparatus may be configured to take and process scans from the patient's intraoral cavity, which may be used to generate one or more models of the patient's dentition (e.g., 3D models). These models may be stored, processed, transmitted and/or displayed. In some examples the models may be displayed on a screen, and may help guide the user in scanning, e.g., to complete the scan of the dentition. In some examples the intraoral scanning mode may also include monitoring of the scanned image(s) to identify either or both movement out of the subject's oral cavity and/or detection of a finger (e.g., a user's finger), which may trigger switching from the intraoral scanning mode into the finger gesture scanning mode (optionally referred to as finger gesture tracking mode). In the finger gesture scanning mode the apparatus may track the position and/or movement of the user's fingers and may identify one or more command controls based on the user's finger gestures. For example the user may move her fingers in a pinching motion in front of the wand to communicate a zooming out command control for zooming out an image of a 3D model being constructed by the intraoral scanning and displayed on the screen of the intraoral scanner. In some examples, switching between the intraoral scanning mode and the finger gesture scanning mode may be done manually (e.g., by switching a switch or control on the wand). Alternatively or additionally, the switching may be done automatically, e.g., by detecting, in the intraoral scanner, one or more fingers. For example, scanning the user's finger gesture may comprise forming a 3D model of at least a portion of a user's fingers.

Thus, any of these methods (or an apparatus for performing them) may include identifying the user's finger gesture with the same intraoral scanner. For example, identifying may include determining the user's finger positions.

The methods described herein may include displaying the user's finger gesture and/or the command control identified by the finger gesture on a display of the intraoral scanning system. This may provide a training tool and may also allow confirming of the command controls. Examples of command controls may include: zoom in, zoom out, translate, and rotate (e.g., which may act on an image on the display). Other command controls may adjust operational parameters of the apparatus, for example: scan rate, scan type, turn on/off, save/transmit/receive data or instructions, switch scanning modes (e.g., visible light, IR, florescence, combinations of these), etc. The system may be manually or automatically be switched back from the finger gesture scanning mode to the intraoral scanning mode either manually or automatically (e.g., by placing the wand back towards or in the subject's mouth and/or detecting an intraoral cavity feature, by engaging a control on the wand or system, etc.). During the intraoral scanning mode the scans may not be displayed or stored (e.g., as part of the intraoral scan of the dental arch, and may not contribute towards modeling of the intraoral arch; finger scans may be separately displayed, interpreted and/or stored, as described herein.

In general, both the subject's intraoral cavity and the user's fingers may be scanned with the same one or more sensors of a wand of the intraoral scanning system. In some examples scanning may include scanning the subject's intraoral cavity (and/or fingers) with structured light. Alternatively, scanning may include scanning by confocal scanning.

The subject's intraoral cavity may be scanned before scanning the user's finger gesture, or vice versa.

As mentioned, in general, these methods may include generating one or more images (e.g., 3D models, etc.) displayed by the system, including during intraoral scanning. In some examples, the command controls may include command controls for modifying a displayed image of the subject's dentition, such as the 3D model. These command controls may be executed on the screen, allowing the user to move, enlarge/shrink, rotate and/or select regions of the 3D model of the dentition as it is being scanned, without having to touch an input such as a screen or keyboard.

As mentioned, also described herein are systems configured to perform any or all of these methods. For example, described herein are intraoral scanning systems that may include: a wand configured for intraoral scanning; a display; and a controller configured to operate the intraoral scanning system to: scan a subject's intraoral cavity with the wand in an intraoral scanning mode and to display a model of the subject's dentition based on the scan; switch from the intraoral scanning mode to a finger gesture scanning mode; scan a user's finger gesture with the wand in the finger gesture scanning mode; and execute a command control based on the user's finger gesture.

For example, the controller may be configured to identify, using the intraoral scanner, the command control from the scan of the user's finger gesture. The user's finger gesture may comprise a position and/or movement of the subject's fingers relative to the intraoral scanner and/or relative to the user's other fingers. In some examples the controller is configured to switch from the intraoral scanning mode to the finger gesture scanning mode when the controller detects one or more fingers in the intraoral scanning mode. For example, the controller may be configured to manually switch from the intraoral scanning mode to the finger gesture scanning mode, or to automatically switch from the intraoral scanning mode to the finger gesture scanning mode.

The controller may be configured display the user's finger gesture and/or the command control on the display.

The system may be configured to use the same wand for scanning the subject's intraoral cavity and the user's fingers gestures. The controller may be configured to form a 3D model of at least a portion of a user's fingers in the finger gesture scanning mode. Any of these systems may include a removable sleeve configured to at least partially cover the wand.

Thus, described herein are methods and apparatuses for using a wand of an intraoral scanner to scan both a subject's intraoral cavity as well as a user's fingers (to determine finger gestures corresponding to control commands). The subject's intraoral cavity may be scanned to form a 3D model (e.g., a digital 3D model) of the intraoral cavity. These methods and apparatuses may store the intraoral cavity data (e.g., the scans and/or the 3D model of intraoral cavity) and the display and/or processing of the images (e.g., the 2D/3D model of the subject's dentition) may be manipulated by the finger gestures. Any appropriate scanning modality may be used, including confocal, structured light, etc.

The methods and apparatuses described herein may help in streamlining the process of treatment planning and design, monitoring and/or well as treatments. These methods and apparatuses may be performed without require the need to use and maintain the sterility of additional input device (e.g., keyboard, mouse, etc.) during the collection of a patient scan or a series of patient scans.

The scanning may occur in either order (e.g., scanning the subject's intraoral cavity first, or tracking finger gestures, or interrupting intraoral scanning to make finger gestures for controlling the display and/or scanning). Scanning the subject's intraoral cavity may include scanning any portion of the subject's intraoral cavity, such as the upper jaw, lower jaw, certain teeth, etc. In some examples the intraoral scan may include separate scans of the upper and lower jaws (teeth, gingiva, etc.). Any scanning modality may be used for scanning the intraoral cavity and/or the user's fingers. For example, scanning the subject's intraoral cavity may comprises scanning with structured light, confocal scanning, near-IR scanning, CT scanning, ultrasound scanning, optical coherence tomography, etc. Scanning the user's fingers is typically done with visible light, and the same light source or a different light source may be used for scanning the intraoral cavity as for scanning the user's fingers. In some examples the user's fingers may be scanned with structured light, confocal scanning, etc.

BRIEF DESCRIPTION OF THE DRAWINGS

The novel features of the apparatuses and methods described herein are set forth with particularity in the claims that follow. A better understanding of the features and advantages of the present invention will be obtained by reference to the following detailed description that sets forth illustrative examples, in which the principles of the invention are utilized, and the accompanying drawings of which:

FIG. 2A shows the wand of the intraoral scanner positioned to detect control gestures, the beginning of a pinching or pinching and rotating gesture as shown in FIGS. 2B-2C.

FIGS. 3A-3I illustrate examples of gestures that may be detected and used as user commands as described herein.

DETAILED DESCRIPTION

Figure 1A:
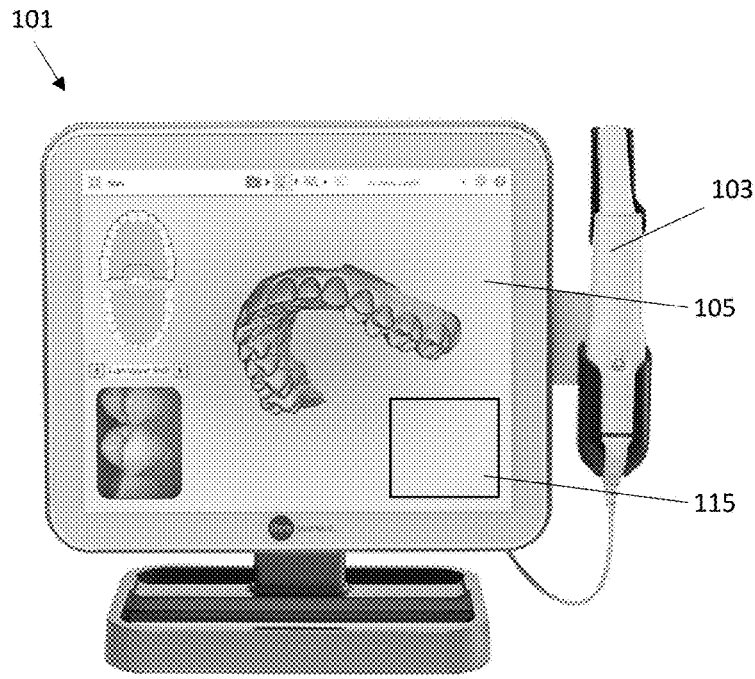
FIG. 1A illustrates one example of an intraoral scanner that may be adapted for used as described herein to perform both intraoral scanning and gesture recognition/commands with the same wand of the intraoral scanner.

In general, described herein are methods and apparatuses for scanning both a subject's oral cavity (e.g., teeth) and scanning a user's hand/fingers and detecting gesture/finger commands with the same intraoral scanner, and in particular with the same wand of an intraoral scanner.

Touchscreen control is now used in most mobile devices, such as mobile phones and tablets, and other computer-based user interfaces. This may include the control of intraoral scanners. When a person uses it with a wet hand or gloved hand, the touch may not work well, and may introduce a possible source of cross-contamination. Gestures are convenient and have a vast interaction space and super high flexibility, providing excellent interactive experience. In particular, it would be beneficial to provide gestural control of optical scanning system, including intraoral scanning systems.

In general, gestures may be detected by any appropriate means, including wearable sensor-based, optical vision-based, electromagnetic sensor-based and ultrasound-based. For example, wearable sensor-based systems may include wearable sensors (such as a "data glove" as an input device, or an accelerometer-based pen-type sensing device). Optical vision-based gesture recognition and ultrasonic-based gesture recognition methods may directly sense the movements of the hand without any wearable device. Ultrasound-based method of gesture recognition may use one or more of: the Doppler effect to sense gestures, an ultrasonic sensor array, and/or ultrasound tracking.

As used herein a gesture, or specifically a hand/finger gesture, may refer to a movement of part of the body, especially a hand and/or fingers, to express an idea or meaning. The movement may be dynamic (e.g., moving the fingers relative to the hand or to the detector(s)/sensor(s), e.g., wand), or it may be static, including holding the hand and/or fingers in a specified pose, position or attitude. Examples of gestures are described herein. These gestures may be associated with a specified command. The associated commands may be context specific; the context may be the current state of the intraoral scanner including the material displayed by a screen on the intraoral scanner.

The gestural control described herein may be used exclusively to control one or more (or all) aspects of the intraoral scanning and/or processing of intraoral scans, or it may be used in conjunction with one or more additional controls, including buttons, knobs, touchscreens, sliders, foot petals, etc. For example, gestural control commands may be used in combination with a control (e.g., button, knob, etc.) on the wand; a first-hand may hold and position the wand with the imaging sensor(s) and may also operate a control on the wand, while the second hand may be used to perform gestural commands or controls. In some examples the wand itself, which may include inertial and/or position sensor(s) may be used as an additional control. For example, the wand may be moved through space with the first hand (holding the wand) while also detecting and using gestural commands generated by the second hand and imaged by the wand in the first hand. Thus, the wand may operate as a 'mouse' or tracking control so that movement of the wand in space may move or otherwise manipulate a cursor or control in the system (e.g., the user interface of the system), such as selecting an operational mode, selecting or manipulating an image or images taken or processed by the intraoral scanning system (e.g., a 2D model, a 3D model, etc.).

In general, the intraoral scanners described herein may include a display, a wand and a controller, which may include one or more processors. For example, FIG. 1A illustrates one example of an intraoral scanner 101 (intraoral scanning system) that may be configured or adapted as described herein to scan both intraoral (e.g., internal features from a subject's oral cavity) and to detect and scan the subject's hand/fingers in order to execute commands encoded in the hand/finger gestures. For example, an intraoral scanner such as the one shown in FIG. 1A may include a handle or wand 103 that can be hand-held by an operator (e.g., dentist, dental hygienist, technician, etc.) and moved over a subject's tooth or teeth to scan intraoral structures. The wand may include one or more sensors (e.g., cameras such as CMOS, CCDs, detectors, etc.) and one or more light sources. The apparatus may also include a display

105 for displaying scanned images, including scanned intraoral images, or processed versions of the scanned images (e.g., 2D images, 3D images, etc.). In some examples the apparatus may be configured to show on the display (or a supplemental display) an image 115 of the hand/fingers detected by the wand of the intraoral scanner and may indicate the gesture and/or command correlated with the gesture.

Figure 1B:
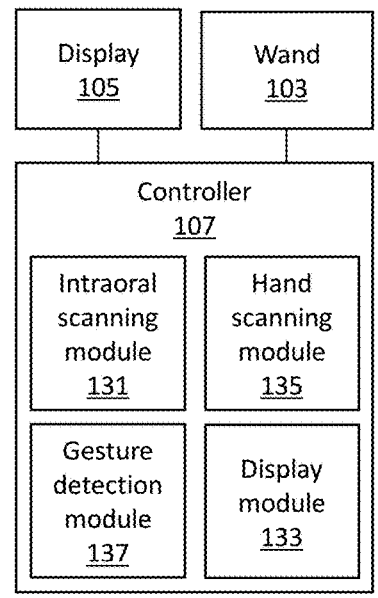
FIG. 1B is a schematic illustration of one examples of an intraoral scanning apparatus as described herein, configured to detect and implement gesture control using the same intraoral scanning wand that may be used for intraoral scanning.

A schematic illustration of an intraoral scanner (intraoral scanning apparatus or system) is shown in FIG. 1B. As mention, the intraoral scanner may include a display 105 and a wand 103; both the display and the wand may be controlled by a controller 107. The controller may be generally configured to control to control data (images) shown on the display, and may control operation of the wand, as well as receive input (data, commands, etc.) from the wand. The controller may include one or more processors and may include software, firmware and/or hardware for implementing and operating intraoral scanning, including controlling the scanning mode (visible light, penetrative wavelengths such as infrared, florescence, etc.), and for processing images scanned by the wand, such as combining images (e.g., forming 3D and/or 2D models images from the scans). The control and/or processing of the intraoral scanning may be handled at least in part by an intraoral scanning module 131, or intraoral scanning processor. In the example shown in FIG. 1B, the controller includes one or more modules or processors that determine or detect when the wand is presented with a gesture, such as a hand and/or finger gesture; for example, the apparatus may include a gesture detection module or processor 137 that can switch the apparatus from an intraoral scanning mode into a gesture detection mode. The apparatus may also include a hand scanning module or processor 135 that may process images to determine finger and/or hand position and may interpret these as command; this module or processor may also confirm the command and/or may execute the command. Additional modules or processors may also be included, such as a display module 133 for displaying one or more images or processed images (including 2D and/or 3D model images) of intraoral scan data and/or detected hand/finger gestures. Other modules or processors may include data storing and/or transmitting modules or processors, and/or wand control modules or processors, etc. The various modules or processors may interconnect and interoperate. For example, the Gesture detection module or processor may toggle between the intraoral scanning module and the hand scanning module.

Figure 1C:
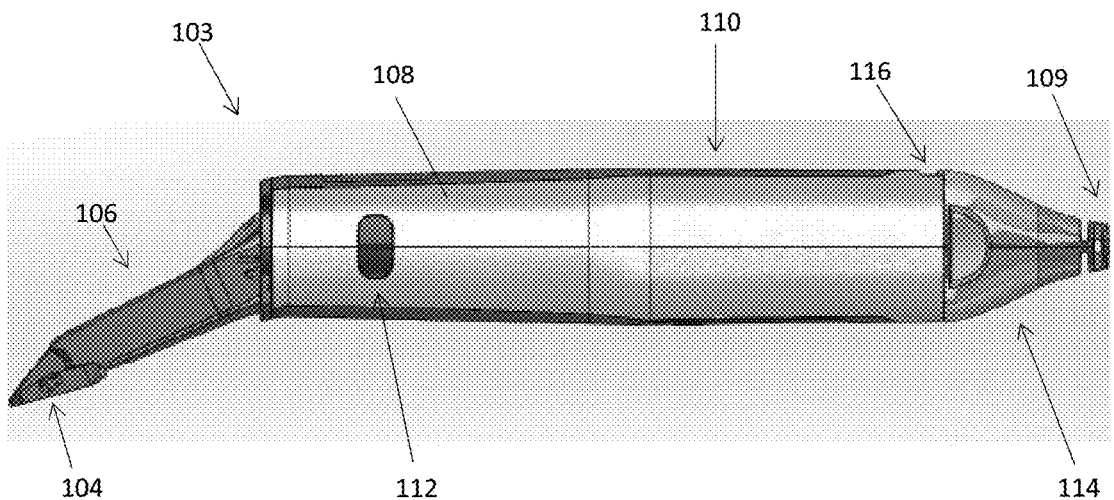
FIG. 1C is an example of one example of a wand of an intraoral scanner as described herein.

FIG. 1C, shows an example of one example of a wand 103. The wand may include one or more light sources configured to emit light (e.g., white light between 400-700 nm, e.g., approximately 400-600 nm, near-IR light, etc.). Separate illumination sources may be used. The light source may be any appropriate light source, including LED, fiber optic, etc. As mentioned above, the wand 103 may include one or more controls (buttons, switching, dials, touch-screens, etc.) 112 to aid in control (e.g., turning the wand on/of, switching between scanning modes, etc.); alternatively or additionally, one or more controls, not shown, may be present on other parts of the intraoral scanner, such as a foot petal, keyboard, console, touchscreen (display 105), etc. The wand may be connected via a cable or wire, or in some examples the wand may be wirelessly connected to the controller and/or display. In some examples the wand is integrated with the controller or portions of the controller.

The wand may include an enclosure or housing that can include internal optical components for taking images of the subject's dentition. The intraoral scanner in FIG. 1A may be configured to take both intraoral scans and hand/finger scans, and may be a handheld scanner that a practitioner can hold and maneuver by hand (e.g., with a single hand). In some examples, the scanner 101 is connected to a power source (not shown) and/or computer via one or more cables (e.g., wires or cords). In some examples, the scanner is configured to send data to a display that displays images of the patient's dentition and/or hand/fingers collected by the scanner. In some cases, the scanner is configured to take two-dimensional and/or three-dimensional images of the dentition and/or hand/fingers. In some examples, the scanner has its own power supply (e.g., battery) and/or wirelessly communicates with a processor.

In this example, the enclosure of the wand and include a main body 108 and a scanning portion 106, which includes one or more optical components 104 (e.g., optical window) that transmit optical signals to and/or from the internal optical components. The scanning portion 106 or probe that can have a shape and size adapted to maneuver around the patient's dentition and position an optical component 104 with respect to the patient's dentition and/or hands/fingers. In some examples, the scanning portion 106 is at a distal end of the scanner 101 with the one or more optical component 104 at one side of the scanning portion 106. In some cases, at least part of the scanning portion 106 may enter into or come near the patient's mouth during an intraoral scanning operation. The scanning portion 106 can be connected to a main body 108 at a non-parallel angle to provide better access and maneuverability around the patient's dentition. The main body 108 can include a handle 110 that is sized and shaped for a practitioner to hold by hand. The main body 108 can include one or more controls 112 (e.g., actuators, buttons, switches, touchpads and/or sliders) for activating one or more functions of the scanner. In some cases, the main body includes one or more vents 116 (e.g., openings) that allow airflow to and from a ventilation component in the internal chamber of the scanner 101 for cooling the internal components of the scanner. In some cases, a proximal end of the main body 108 tapers at cable interface region 114 that couples the cable 109 to the main body 108.

In general, the intraoral scanning apparatuses described herein may be configured to scan very quickly, e.g., at greater than 30 frames per second (fps) (e.g., 40 fps or greater, 50 fps or greater, 80 fps or greater, 100 fps or greater, etc.), and at very high accuracy in 3D. In some examples the intraoral scanner may be configured to use structured light for 3D scanning and/or confocal scanning.

Any of the apparatuses described herein may use the same intraoral scanner (e.g., the same wand, and in some examples the same sensors in the wand) for both intraoral scanning in the oral cavity and for detecting and hand and/or finger gestures. Typically, the user operating the scanner may therefore seamlessly switch between intraoral scanning an interfacing with the apparatus through finger gestures. For example, a user may begin scanning a subject's intraoral cavity with the wand, and my then remove the wand from the subject's mouth to direct it to the fingers of one of the user's hands. The apparatus may then detect when the wand is removed from the mouth and/or may detect that fingers are being imaged; the apparatus may then toggle from an intraoral scanning mode to a gesture-detection mode. The user may then return to scanning (or may end the scanning). Thus, the user may scan, stop and interface the application, then continue scanning, and this may be repeated multiple times.

In some examples the intraoral scanners described herein may have a FOV and small depth of scan that is sufficiently large and deep to detect both the intraoral detection of teeth (e.g., between 0.1 and 40 mm) and the hand/fingers (e.g., between 10-150 mm). Alternatively or additionally, the apparatuses described herein may switch between a smaller field depth of scan (e.g., between 0.1 and 40 mm, between 1 and 40 mm, between 1 and 30 mm, etc.) and an intermediate or larger depth of scan (e.g., between 10-150 mm, between 20 and 150 mm, etc.). Switching may include switching between different sensor in the wand and/or applying/inserting different lenses, filters, etc. For example, in some examples the optical path for intraoral scanning of the dentition may be different for scanning the hand/fingers; in some examples the optical path for intraoral scanning of the dentition may be the same as for scanning the hand/fingers. The wand 103, and particularly the scanning portion of the wand, may include a first optical path for scanning the intraoral cavity, e.g., teeth gingiva, etc. The first optical path may include one or more lenses, and a sensor configured to receive images of the teeth gingiva.

In some examples the intraoral scanner, including the sensors on the wand, may be configured for intraoral 3D camera function. The depth of scan may be 30 mm or greater and the capture rate may be greater than 20 fps. As mentioned above, in some examples the system may be configured so that it may display an image or rendering of the hand/fingers once detected (or may indicate that they are too far or too close to the wand sensors). For example, to help usage and training, a view of the captured fingers may be displayed on small window (e.g. of the display) to guide the user to be in valid range of FOV and depth. In some examples an icon of the gesture being detected may be displayed in a window on the display (the same or a different window). Once a user has mastered the positioning and hand signals, the window(s) may be hidden.

Figure 2A:
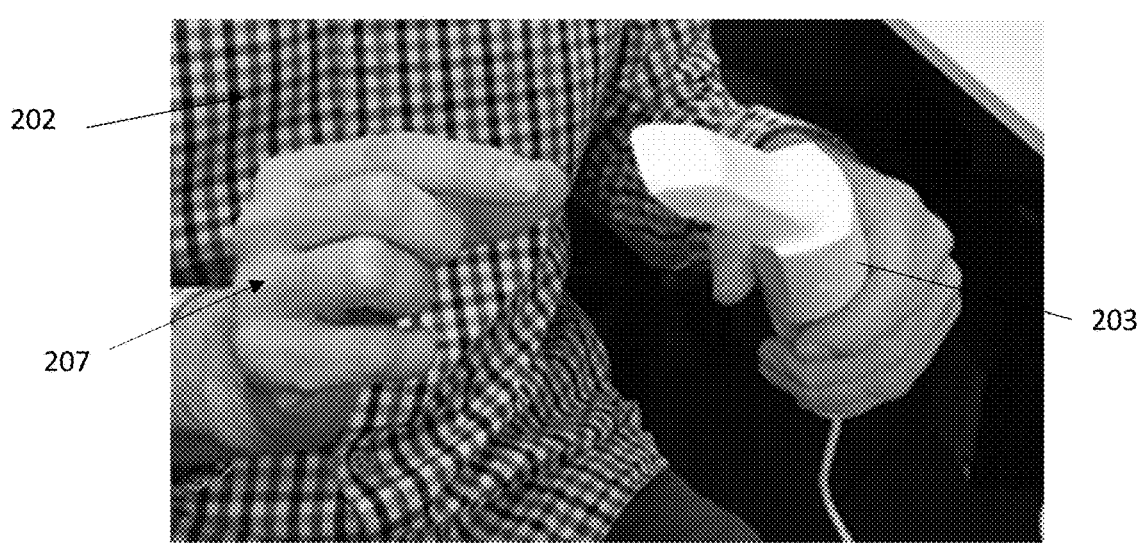
FIGS. 2A-2C illustrate the use of an intraoral scanner with single-handed gesture control as described herein.
Figure 2B:
Figure 2C:
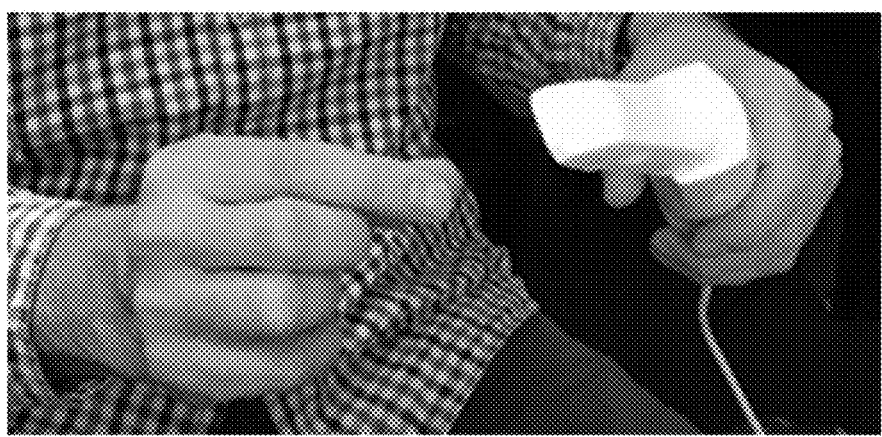

FIGS. 2A-2C illustrate one example of the use or operation of an apparatus for detecting and using gestural control as described herein. In this example the user 202 holds the wand 203 in one hand and may form finger gestures with the other hand 207, while directing the sensors of the wand to image the fingers making the gestures. The apparatus may detect the fingers and finger gestures as the user either holds a finger gesture (pose) or continues with the gesture, as shown in FIGS. 2B-2C. The apparatus may provide feedback confirming that the gesture has been detected and may execute one or more control operations based on the gestures. For example, the control gestures may be used when visualizing the scans, including visualizing the renderings, such as a 2D or 3D reconstruction of the dentition being scanned. The user may gesture to virtually "grab" the reconstruction and may then move their fingers to drag, rotate or otherwise change the relative position of the reconstruction on the display. For example a pinching gesture may be used to 'grab' or select an image of a 3D model on the screen, and a twisting or movement of the pinched fingers may change the relative angle or position of the 3D model on the display screen. The use may alternate between scanning of the intraoral cavity, e.g., by moving the wand over the teeth and gingiva or other oral structures, and/or may move the apparatus out of the mouth and scanning the fingers to detect control gestures. In some example, the wand may be configured switch between intraoral scanning and hand/finger scanning. For example, the wand may be configured to scan the patient's fingers to detect and/or identify gestures before, during or after scanning the intraoral cavity.

A wand of an intraoral scanner may generally be adapted for scanning both an intraoral cavity and a subject's fingers. For example, a wand may include an illumination source (e.g., light), one or more image sensors, and additional optical elements, such as lenses, filters, polarizers, beam splitters, etc. The illumination unit (e.g., light, such as white light, laser, etc.) may illuminate the field of view to be imaged, including the teeth, fingers, etc., in light wavelength appropriate for imaging. In some examples the wand is configured to use 3D imaging (e.g., using structured light). The illumination unit may be an LED and/or a laser. The same illumination source may be used for both intraoral scanning and/or hand/finger scanning. Alternatively, in some examples, separate light sources may be used. Different imaging modalities may be used, including visible light, near-IR light, or different wavelengths of light, etc. In some examples intraoral scanning may be done with a separate optical path than hand/finger scanning; in some examples the same optical path may be used, or a modified optical path (using some of the common optical path) may be used.

As mentioned, the intraoral scanner may be configured for intraoral scanning using structured light, e.g., for three-dimensional scanning using structured light techniques and/or light-field technology. A pattern (static and/or time-varying) that may be used with any of these apparatuses and methods may be configured for providing structured light imaging by projecting the known pattern (e.g., spots, grids, lines, bars, e.g., horizontal bars, arrays, etc.) and analyzing the manner in the pattern deforms when striking the target surface(s). The apparatus may calculate the depth and surface information of the object(s) in the scene. Thus, any of these apparatuses may be configured as structured light 3D scanners. For example, the intraoral scanning may include structured light scanning. In some examples the wavelengths of light used may be different, and different patterns of light may be applied corresponding to the different wavelengths. For example, visible and/or infrared light may be used. Any of these apparatuses may be configured as "invisible" or "imperceptible" structured light apparatuses, in which structured light is used simultaneously or concurrently without interfering with imaging at different frequencies. For example, infrared light and visible light may be applied and detected at high (including extremely high) frame rates that alternate between two different patterns. The patterns may be complimentary or opposite (e.g., in which the dark regions in a first pattern are illuminated in the second pattern). Different wavelengths of visible light may be used instead or in addition to infrared light. In some examples, structured light may be used for imaging the hand/fingers, and/or for both intraoral imaging and hand/finger imaging, which may provide three-dimensional data that may be used to reconstruct the 3D volume of the teeth in intraoral scanning modes and for detecting finger position and gestures in the gestural detection mode.

Any of these apparatuses may include a sleeve or sleeves for use with (or over) the wand. Thus, the optical path of the wand may include a part of a sleeve, cover, attachment, etc. that may be removably placed onto the wand and used for scanning. The fit between the sleeve and the wand may be snug so that the second optical path is coupled to the first optical path. In some examples the sleeve (or cover, adapter, etc.) may be secured by an attachment such as a snap, clasp, etc.; in some examples the sleeve (or cover, adapter, etc.) may be secured by a friction fit. The sleeve, attachment, cover, etc. may including an indicator indicating that it is properly attached. The indicator may be visible (e.g., a color indicator, etc.) audible, tactile, etc. (a click, snap, etc.). In any of the apparatuses described herein a contact or connection indicator may be included to indicate contact or connection between the wand and a sleeve, which may allow detection of the sleeve by the system. For example, connection or contact indicator may include an electrical contact, a magnetic contact, a capacitance detector, etc. to allow detection of the sleeve by the system.

As mentioned in some examples the apparatuses described herein may be configured for use with a Multi structured light (MSL) scanner for 3D scanning.

In some examples, the apparatus may provide illumination when imaging the hand/fingers as well as the teeth. For example, the illumination may be a high-speed sequence of short flashes image captures each will low exposure, which may then be summed. 3D imaging of the hand/fingers may be done using available (e.g., ambient, clinical, user-provided) light or using the overhead dentist illumination lamp. Alternatively, as mentioned above, in some examples suitable illumination conditions may be achieved by including lighting in the intraoral scanner, e.g., LEDs, etc. Image processing algorithms may dynamically optimize the light conditions based on the cameras captured image. In some examples, some or all of the illuminating elements (possibly combined with the sleeve optics) may be used to generate a visible pattern on the subject's hand/fingers to assist the user with positioning the wand in the optimal position and orientation. Available structured light illumination may be used for 3D image capture of the hand/fingers.

Gestures

The apparatuses described herein may be configured to detect and use (e.g., as commands, controls, etc.) any appropriate gesture. FIGS. 3A-I illustrate examples of finger gestures that may be detected by the apparatus and may be used to control or otherwise manipulate the apparatus, including manipulating the scanned images and/or controlling operation of the intraoral scanner apparatus. FIG. 3A shows a finger pinching or closing gesture, in which the thumb and index finger are moved together. This gesture may be used, for example, to zoom or enlarge in the context of manipulating an image or images (e.g., 3D model of the dentition). FIG. 3B describes a finger opening gesture, in which the thumb and index finger are moved apart. This gesture may be used, for example, to shrink or reduce in the context of manipulating an image or images (e.g., 3D model of the dentition). FIG. 3C illustrates a clockwise movement in which the index finger is rotated clockwise. This gesture may be used, for example, to rotate an image or part of an image clockwise in the context of manipulating an image or images (e.g., 3D model of the dentition). FIG. 3D illustrates a counterclockwise movement in which the index finger is rotated counterclockwise. This gesture may be used, for example, to rotate an image or part of an image counterclockwise in the context of manipulating an image or images (e.g., 3D model of the dentition). FIG. 3E illustrates a sliding movement in which the thumb is moved along the index finger, as shown. FIG. 3F illustrates a downward movement/upward movement gesture, in which the index finger is bent to move up and down relative to the thumb. FIG. 3G shows a side-to-side gesture in which the index finger is wagged side to side. FIG. 3H shows another example of an upward and downward movement gesture, in which the index and middle fingers are bent to move up and down relative to the thumb. FIG. 3I shows a rotating gesture in which the wrist is rotated to rotate all of the fingers about the midline from the wrist. As mentioned, virtually any combination of gestures, including compound movements or isolated movements of the fingers and/or wrist may be detected and may correlated to one or more commands and controls. In some examples, these gestures may exclude big movements of the palms or arms. In general, unless the context specifies otherwise, a user's thumb may be considered as one of the user's fingers. In some examples the context may indicate that the user's thumb may be considered separately from the user's other fingers (e.g., relative movement between the thumb and the user's fingers may refer to relative moment between the user's thumb and other fingers).

The gesture identification and control sub-system of the intraoral scanners, which are described herein, may provide numerous advantages, including allowing control of the operation of the apparatus and/or manipulation of data (images, models, etc.) scanned by the apparatus without touching and therefore risking cross-contamination, as well as allowing the user to provide this control from virtually any location while holding the wand. The gesture detection may be performed wherever the user holds the wand, regardless of how far the user is from the display and/or controller. The gesture identification and control sub-systems may be easily and readily integrated into an intraoral scanner and use the optical path (e.g., sensor, lenses, etc.) used for the intraoral scanning portion of the apparatus. These systems may therefore prevent or reduce the likelihood of cross-contamination and may also reduce wear-and-tear of the display, as the user does not need to touch the display.

Methods

Figure 4:
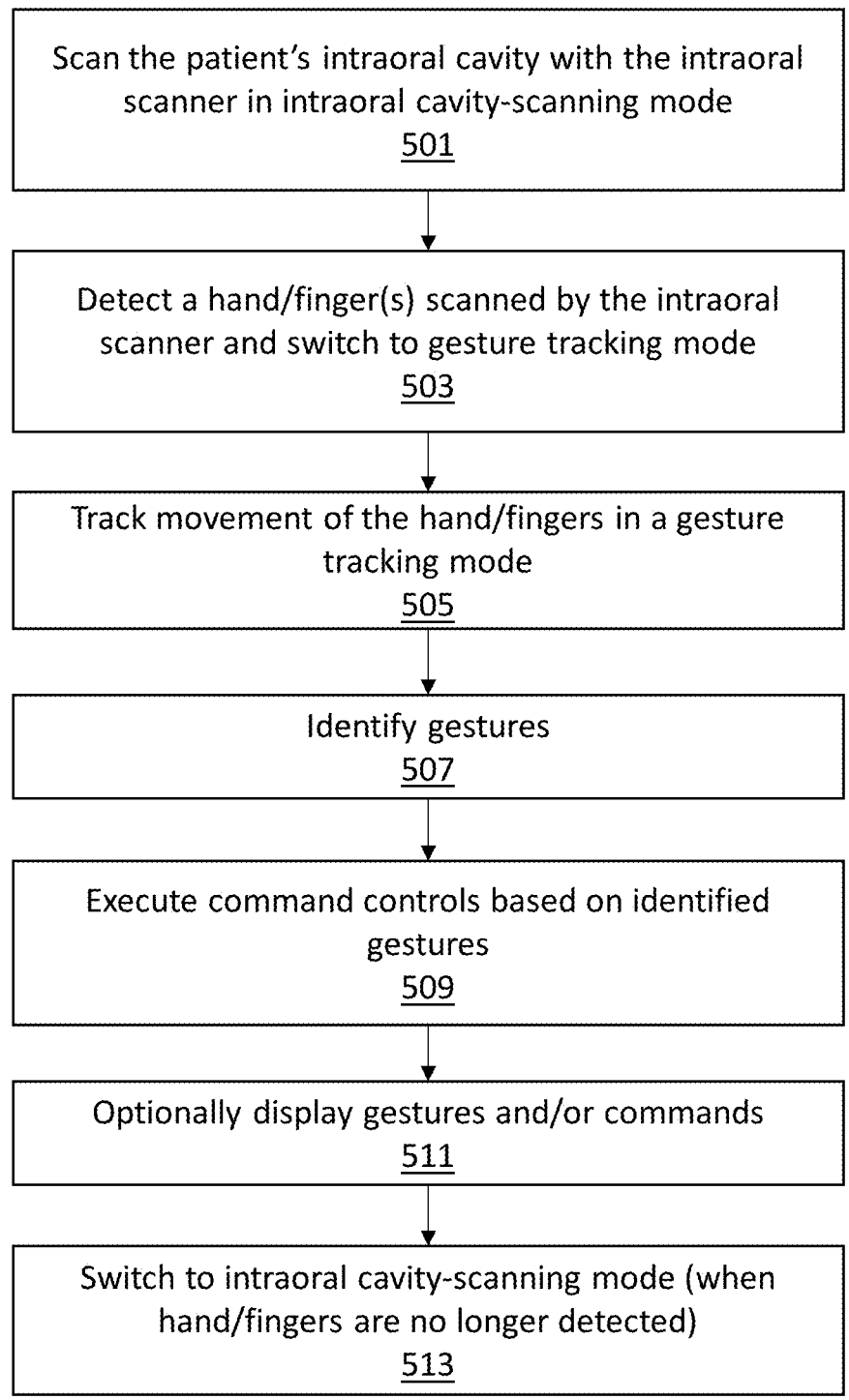
FIG. 4 is one example of a method of using gestural controls for an intraoral scanning apparatus as described herein.

In general, the apparatuses described herein may detect gestures and may use these detected gestures to control or manipulate the intraoral scanner and/or the data collected by the intraoral scanner, such as images or models constructed from images of the subject's dentition (e.g., teeth, gingiva, palate, etc.). FIG. 4 illustrates one example of a method for operating an intraoral scanner including a gesture identification and control sub-system as described above. In use, the apparatus may scan the patient's intraoral cavity (e.g., teeth, gingiva, etc.) using the intraoral scanner 501 operating in an intraoral scanning mode. Prior to scanning one or more controls may be used to control scanning settings; these controls may include using hand/finger gestures. The apparatus may toggle between intraoral scanning mode and a finger gesture scanning mode (during which the apparatus recognizes finger gestures) either manually, e.g., by toggling a control such as a button or switch, or automatically, e.g., by detecting that the device has been removed from the oral cavity and/or by identifying a hand or finger within the field of view 503. In some examples the wand may include an accelerometer or other position-detection hardware, firmware or software that may determine when the apparatus is outside of the patient's mouth.

The apparatus may operate in the gesture tracking mode 505 to track the movement of the hand and/or fingers. Finger tracking may include identifying the amount of time (dwell time) that the fingers/hand remains in approximately the same pose and may track the movements of the fingers/hand relative to the other fingers and/or relative to the wand. The apparatus may identify the individual fingers and generate a model, such as a wireframe model, of their positions and movements. The apparatus may also identify gestures 507 from this data collected during the gesture tracking mode. In some example the apparatus may include a gesture identification processor or model that may identify, based on the position and/or relative movements of the fingers. In some examples the system may be trained to identify gestures and on identifying relative finger positions to determine gestures.

Gestures may be associated with any command, instruction, input or control. In some example the interpretation of the gesture may be conditional, based on the status of the intraoral scanning apparatus. For example during scanning, if an image or display of the scanning images are being shown, such as by a 3D model or rendering being constructed, certain gestures may be associated with control of the display, such as rotating, scaling (enlarging/shrinking), tilting, clearing/resetting, etc. In other context (e.g., prior to starting scanning or after completing a scan), the same or different gestures may be interpreted to have different command controls. For example, setting scan rates, scanning conditions, selecting from menu or text items, etc.

Any of the identified interpreted gestures may then be used to execute the command associated with the identified gesture 509. The command associated with the gesture may be immediately executed, or it may be executed after a verification step. For example, the apparatus may verify the gesture and/or the command associated with the gesture.

In any of the apparatuses described herein, the apparatus (e.g., the controller) may be adapted to display the hand/finger movements (gestures) and/or the interpretation of the hand/finger movements 511, and/or the command associated with the hand/finger movements. The display may be continuous and in real time. As described above, in some examples, the apparatus may display the gesture and/or associated command(s) in a region of the screen either continuously or intermittently.

The apparatus may switch from the gesture-detection mode back to an intraoral-cavity scanning mode when it no longer detects the user's fingers/hand 513.

As mentioned above, any number of gestures and/or associated commands may be used. In some example a minimal number (e.g., 3-8, 3-7, 3-6, 3-5, 2-8, 2-7, 2-6, 2-5, etc.) of gestures may be used/identified and may be associated with a small set of command instructions. For example, in some examples the apparatus may be configured to recognize simple gestures, such as finger pinching, rotation, etc. The associated commands may be a small subset that focuses on control of the display (e.g., control of the display of the 3D visual model being formed). For example, the associated commands may include: zoom (zoom in/zoom out), translation (e.g., moving in x, y and in some examples z), and/or rotation (in pitch, roll, and/or yaw).

In some examples the apparatus, and particularly the portion of the apparatus that interprets gestures, typically including the controller and one or more sub-system, may be configured to detect or be limited to detecting the relative movement. For example, both the wand and the hand making gestures may be moving, but apparatus may see only relative motion between them. Thus in some examples it may be preferable, to ignore wand motion. This may be done by looking at the wand IMU, and ignoring self-motion.

The methods and apparatuses described herein may include methods of scanning and/or modeling both a subject's intraoral cavity and/or, for scanning both a subject's dentition and for scanning fingers and detecting finger gestures as described herein. Once the intraoral scanner is used to scan within the subject's mouth (intraorally), the same wand of the intraoral scanner may be used to scan the hand/fingers of the dental appliance, without requiring sterilization or intermediate steps, while preventing or eliminating cross-contamination. The user (e.g., dentist, technician, orthodontist, etc.) may operate a switch, control, toggle, etc. on or affiliated with the intraoral scanner, e.g., the handle portion of the wand, to switch between scanning the intraoral cavity and using the wand in a finger (or gesture) scanning mode. The scan data (and particularly data for the intraoral scanning, but in some examples and may be taken and stored by the intraoral scanner, either with or without additional processing. For example, in some examples these methods may include storing and/or transmitting a subject's digital scanning. The patient-specific data may be stored in a data structure that may combine both the intraoral scanning 3D.

Any of the methods described herein may include methods of generating a digital model of both the intraoral cavity and the user's fingers/hand. For example, scanning both the intraoral cavity and a user's fingers may be scanned with an intraoral cavity scanning device. In some examples, the device can be configured for any scanning modality for the intraoral cavity: confocal, structured light, near-IR, ultrasound, etc. As mentioned above, the scanning may be 2D scanning or 3D scanning. In some examples the gestural (e.g., finger/hand) scanning may be done using the same intraoral scanner (e.g., same cameras/sensors and/or imaging sources, such as laser, light, etc., as for intraoral scanner, using adaptive optics to change the depth of focus) or in some examples a separate camera(s) on the scanner and/or a sleeve may be used.

In general, the gesture recognition may be performed to scan in 2D or 3D. As mentioned, in some examples the fingers/hand may be scanned using the same camera and/or imaging source: For example, the hand/fingers may be scanned using different camera and imaging source: new optics on a sleeve, on wand, or protective sleeve etc.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and examples such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific examples in which the subject matter may be practiced. As mentioned, other examples may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or variations of various examples. Combinations of the above examples, and other examples not specifically described herein, will be apparent to those of skill in the art upon reviewing the above description.

What is claimed is:

1. A method comprising:
scanning a subject's intraoral cavity with a scanning portion of an intraoral scanner of an intraoral scanning system in an intraoral scanning mode, the scanning portion extending from a handle portion of the intraoral scanner and including one or more optical components;
switching from the intraoral scanning mode to a finger gesture scanning mode, wherein switching to the finger gesture scanning mode disables the intraoral scanning mode;
orienting the scanning portion toward one or more fingers of a user;
detecting movement of the one or more fingers of the user relative to the scanning portion using the scanning portion with the system in the finger gesture scanning mode without touching the user's one or more fingers to the intraoral scanner; and executing a command control with the intraoral scanning system encoded by the detected movement of the one or more fingers.

2. The method of claim 1, further comprising detecting, using the intraoral scanner, the command control from the detected movement of the one or more fingers.

3. The method of claim 1, wherein the movement comprises a position, a movement or a position and a movement of the user's one or more fingers.

4. The method of claim 1, further comprising identifying the movement of the one or more fingers of the user with the intraoral scanner.

5. The method of claim 1, further comprising displaying a gesture based on the detected movement, the command control, or the gesture and the command control on a display of the intraoral scanning system.

6. The method of claim 1, wherein the command control comprises one of: zoom in, zoom out, translate, and rotate.

7. The method of claim 1, wherein the command control comprises a control modifying a displayed image of the subject's dentition.

8. An intraoral scanning system, the system comprising:
a wand configured for intraoral scanning;
a display; and
a controller configured to operate the intraoral scanning system to:
scan a subject's intraoral cavity with the wand in an intraoral scanning mode and to display a model of the subject's dentition based on the scan;
switch from the intraoral scanning mode to a finger gesture scanning mode in which the system is adapted to detect non-contact motion of one or more of a user's fingers relative to the wand, wherein switching to the finger gesture scanning mode disables the intraoral scanning mode;
scan, with a non-contact optical component, a user's finger gesture with the wand in the finger gesture scanning mode; and
execute a command control based on the user's finger gesture.

9. The system of claim 8, wherein the controller is further configured to identify the command control from the scan of the user's finger gesture.

10. The system of claim 8, wherein the user's finger gesture comprises a position, a movement, or the position and the movement of the user's fingers.

11. The system of claim 8, wherein the controller is configured to switch from the intraoral scanning mode to the finger gesture scanning mode when the controller detects one or more fingers in the intraoral scanning mode.

12. The system of claim 8, wherein the controller is configured to manually switch from the intraoral scanning mode to the finger gesture scanning mode.

13. The system of claim 8, wherein the controller is configured to display the user's finger gesture, the command control, or the user's finger gesture and command control on the display.

14. The system of claim 8, wherein the command control comprises one of:
zoom in, zoom out, translate, and rotate.

15. The system of claim 8, wherein the command control comprises a control modifying a displayed image of the subject's dentition.

16. The system of claim 8, further comprising a control configured to switch between intraoral scanning mode and the finger gesture scanning mode.

17. The system of claim 8, further comprising a removable sleeve configured to at least partially cover the wand.

18. An intraoral scanning system, the system comprising:
a wand configured for intraoral scanning;
a display; and
a controller configured to operate the intraoral scanning system to:
scan a subject's intraoral cavity with the wand in an intraoral scanning mode and to display a model of the subject's dentition based on the intraoral scan;
switch from the intraoral scanning mode to a finger gesture scanning mode in which the system is adapted to detect a non-contact movement of one or more of a user's fingers relative to the wand, wherein switching from the intraoral scanning mode to the finger gesture scanning mode renders the intraoral scanning mode inactive;
scan, with a non-contact optical component of the wand, a user's finger movement relative to the wand with the wand in the finger gesture scanning mode; and
execute a command control based on the user's finger movement.

19. The system of claim 18, wherein the controller is further configured to identify the command control based on the detected non-contact movement of the one or more fingers relative to the wand.

20. The system of claim 18, wherein the controller is configured to switch from the intraoral scanning mode to the finger gesture scanning mode when the controller detects one or more fingers in the intraoral scanning mode.

* * * * *